United States Patent [19]

Cline et al.

[11] Patent Number: 5,458,126
[45] Date of Patent: Oct. 17, 1995

[54] CARDIAC FUNCTIONAL ANALYSIS SYSTEM EMPLOYING GRADIENT IMAGE SEGMENTATION

[75] Inventors: Harvey E. Cline, Schenectady; William E. Lorensen, Ballston Lake, both of N.Y.

[73] Assignee: General Electric Company, Schenectady, N.Y.

[21] Appl. No.: 201,440

[22] Filed: Feb. 24, 1994

[51] Int. Cl.$^6$ ............................................. A61B 5/05
[52] U.S. Cl. ................... 128/653.1; 324/309; 395/129
[58] Field of Search .............. 128/653.1; 364/413.13; 395/129; 324/309

[56] References Cited

U.S. PATENT DOCUMENTS

| | | | |
|---|---|---|---|
| 4,547,892 | 10/1985 | Richey et al. | 128/653.1 |
| 4,936,311 | 6/1990 | Oe | 128/653.1 |
| 5,111,820 | 5/1992 | Axel et al. | 324/309 |
| 5,187,658 | 2/1993 | Cline et al. | 364/413.13 |
| 5,204,625 | 4/1993 | Cline et al. | 324/309 |
| 5,361,763 | 11/1994 | Kao et al. | 128/653.1 |

OTHER PUBLICATIONS

U.S. patent application: "Gradient Image Segmentation Method" by H. E. Cline and W. E. Lorensen.
U.S. patent application: "Cardiac Functional Analysis System Employing Gradient Image Segmentation" by H. E. Cline and W. E. Lorensen.
Publication: "3D Reconstruction of the Brain from Magnetic Resonance Images Using a Connectivity Algorithm", by H. E. Cline et al., published in Magnetic Resonance Imaging, vol. 5, No. 5, pp. 345–352, 1987.
Publication: "Three–Dimensoinal Segmentation of MR Images of the Head Using Probability and Connectivity", Harvey E. Cline, et al., Journal of Computer Assisted Tomography, vol. 14, No. 6, Nov./Dec. 1990, pp. 1037–1045.

*Primary Examiner*—William E. Kamm
*Assistant Examiner*—Brian L. Casler
*Attorney, Agent, or Firm*—Lawrence P. Zale; Marvin Snyder

[57] ABSTRACT

A non-invasive imaging device obtains a four dimensional (4D) image data set of a living subject representing three dimensions and time in relation to the subject's cardiac cycle. In order to determine various vascular parameters, it is useful to segment the image data set into internal structures defined as having the same tissue types contiguous locations. To accomplish this, a gradient calculation unit constructs a gradient data set from the image data set indicating the magnitude of spatial changes in the image data set. A plurality of locations are selected by an operator with a pointing device during 'training' along with corresponding data values in the image and gradient data sets. These data values are plotted by a scatter generator against each other to construct a scatter plot then processed to determine a bivariate statistical probability distribution. The remaining data values are then assigned a tissue type based upon their plot on the bivariate statistical probability distribution. Contiguous locations having the same tissue type assignment are identified as a solid structure by a connectivity calculator. These solid structures may be the internal volume of cardiac chambers. Since these volumes may be accurately measured over the cardiac cycle, a functionality calculator determines vascular functionality, such as ejection fraction, and cardiac output and displays the results on a monitor to the operator.

5 Claims, 3 Drawing Sheets

CARDIAC FUNCTIONAL ANALYSIS SYSTEM EMPLOYING GRADIENT IMAGE SEGMENTATION

CROSS REFERENCE TO RELATED APPLICATIONS

This application is related to U.S. Patent application "Gradient Image Segmentation Method" Ser. No. 08/121,628, filed Sep. 16, 1993; and "Cardiac Functional Analysis Method Using the Gradient Image Segmentation" Ser. No. 08/201,443, filed Feb. 24, 1994 both by Cline, Lorensen, both assigned to the present assignee and both hereby incorporated by reference.

BACKGROUND OF THE INVENTION

1. Field of the Invention

This invention relates to systems for determining cardiac functionality within a living subject, and, more particularly, to systems for calculating cardiac functionality from four dimensional data employing tissue segmentation.

2. Description of Related Art

Typically blood flow and cardiac function in living subjects has been analyzed with ultrasound, X-ray and computed axial tomography (CAT) with contrast agents, magnetic resonance (MR) imaging and other various modalities. Blood velocity, a quantitative measure of blood flow through vessels, cardiac ejection fraction (the ratio of ventricle chamber volume of relaxation vs. contraction), total cardiac output, and cardiac enlargement are parameters of interest which are significant in determining cardiac disease and failure.

Past techniques measure flow by determining blood velocity, by ultrasound doppler methods, for example, and then, vessel cross sectional area and calculate blood flow rates.

Methods for determining volumes of cardiac chambers, for instance, involve cardiac gating and two or three dimensional imaging. These may be MR, CAT scans, even positron emission tomography (PET). The areas of interest of a slice of data obtained at a specific time during the cardiac cycle are traced by hand by an operator on a computer screen for each image slice, and for all cardiac time instants of interest. This is inaccurate since the boundary between the inside of the chamber and the chamber wall may be obscured since the contrast may not be so great.

Presently there is a need for a non-invasive method of accurately determining cardiac functionality.

OBJECTS OF THE INVENTION

Accordingly, an object of the present invention is to provide a non-invasive system of accurately determining cardiac functionality.

Another object of the invention is to provide a system for accurately identifying and displaying interfaces between different structures of moving tissue, stationery tissue, and flowing fluids.

SUMMARY OF THE INVENTION

In accordance with present invention, a 4-dimensional (4D) data set of internal structures of a living subject is obtained, 3 spatial dimensions, and a time dimension gated with a periodic motion such as a cardiac cycle. The 4D image data set is processed by a gradient method to determine locations of significant change, which are stored as a 4D gradient data set. An operator selects locations distributed more or less uniformly over each of the tissues of interest on an image of a slice (y) of the subject at a cardiac time (t) displayed on a computer screen. These selected locations correspond to a set of sample data points of both the 4D image data set and the 4D gradient data set. The intensities of the two data sets are plotted against each other to produce clusters of data points, known as a scatter plot identifying different tissue classes. The selected data points are then used to calculate a bivariate probability distribution of the tissue intensities. This probability distribution, and scatter plot are then used to generate a feature map comprising an array of the most probable tissue identification for all remaining data points. The feature map is the stored result of the most probable tissue type for all remaining points for this slice of the image data set. This process is then repeated for all slices of interest and for all cardiac times (t) of interest resulting in a tissue type being assigned to each desired image data set location, of each desired cardiac time instant (t).

Once the locations of the 4D data set have been assigned a tissue type, the assignments can be smoothed to remove misclassified data points and to provide a smoothly varying surface normal vector which may be used for gradient shading.

A connectivity algorithm can then be used to identify contiguous locations of similar tissue types, being a structure.

The volume within a defined structure may now be accurately identified and used in calculation of ventricle volume over cardiac cycle, ejection ratio, cardiac output etc. This volume may be determined by determining a sum of cross sectional area over different slices, spaced by a known slice width.

The segmented structures may also be color coded to visually identify different structures, such as moving fluid, moving tissue, and stationery tissue. Surface gradient shading can be used to improve the appearance of the display.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawing(s) in which:

To facilitate reader understanding, identical reference numerals are used to designate elements common to the

DETAILED DESCRIPTION OF A PREFERRED EMBODIMENT

Figure 1:
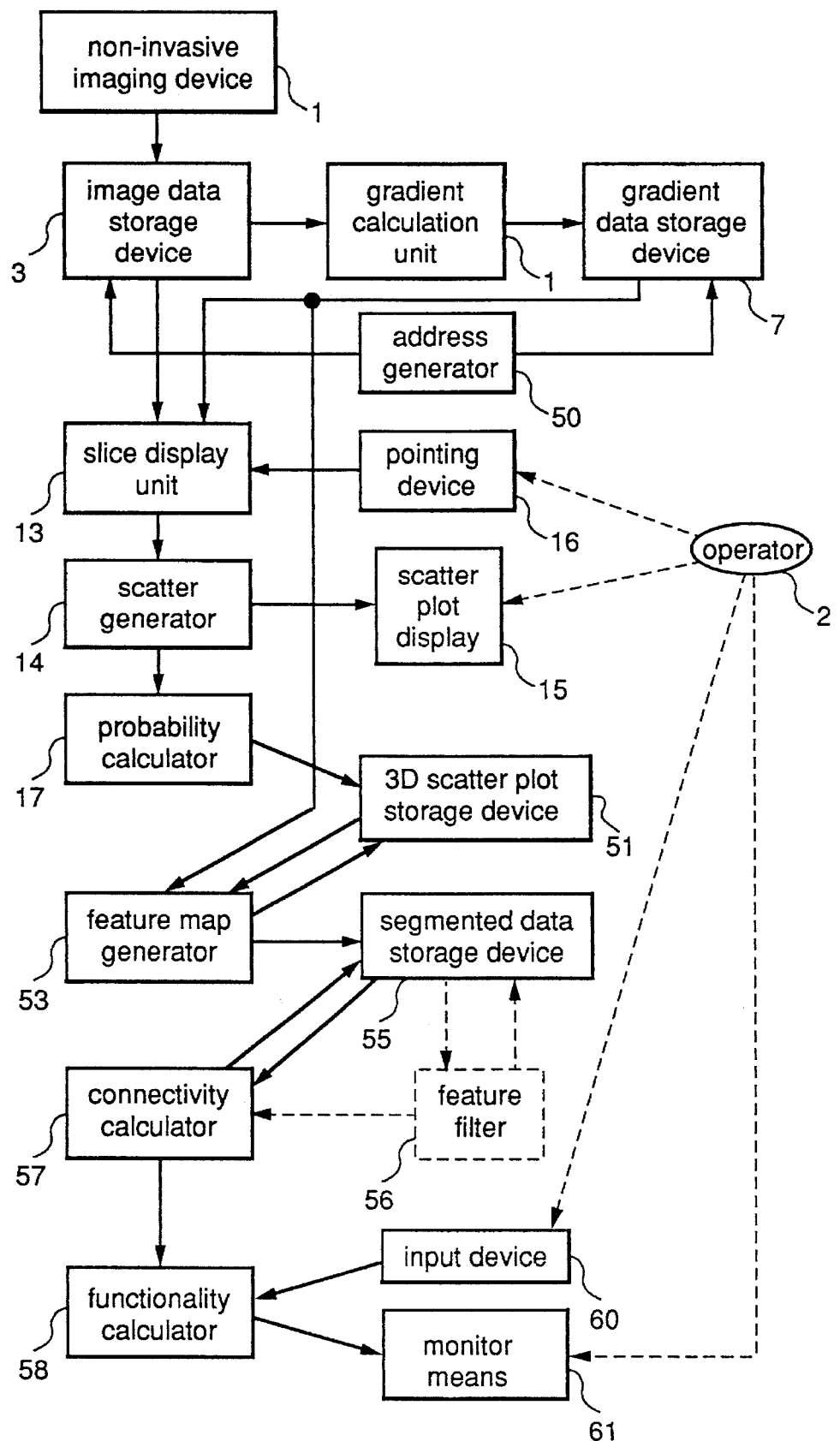
FIG. 1 is a block diagram of a vascular functionality measurement system in accordance with the present invention.

FIG. 1 is a block diagram of a vascular functionality measurement system in accordance with the present invention, comprising a non-invasive imaging device 1 such as an x-ray computed axial tomography (CAT) scan apparatus, a nuclear magnetic resonance (NMR) imaging device, or any other nonintrusive data gathering apparatus, which nonintrusively acquires data from a subject. The data acquisition is gated with the subjects cardiac cycle in which a 3D data set is acquired during the cardiac time instant (t) with each data value of the data set pertaining to a physical property of the Subject at a location (x,y,z), thereby resulting in a 4D data set, (x,y,z,t). An image data storage device 3 is provided to store the 4D data set. A gradient calculation unit 5, calculates changes in the values of the 4D data set entries from location to location, identifying boundaries of significant change. If the entries represent physical parameter of a location, the changes represent a spatial gradient of the physical property.

Gradient calculation unit 5 produces a gradient data set having 4 dimensions representing the changes in the image data set over space for all cardiac time instances (t). The gradient data set is stored in gradient data storage device, 7.

During "training", a slice display unit 13 displays a selected planar slice image to an operator 2, for any selected cardiac time instant (t) from the data storage devices. It is preferred to select a slice in the middle of the image data set with respect to both position and cardiac time instant (t). In an alternative embodiment, a gradient image from the same location and cardiac time instant may also be shown, either side-by-side or superimposed with the slice image. Operator 2, employing a pointing device 16, which may comprise, for example, a light pen or a touch-sensitive screen, selects locations on the slice image characteristic of each of a plurality of tissue types known by the operator based upon the image and the subject's anatomy. The locations are selected uniformly over various known tissue types to provide the clearest differentiation between the tissue types. In a cardiac image, for example, the tissue types may comprise arteries, veins, cardiac muscle, cardiac valves and blood pools.

The data values from the image data set and the gradient data set corresponding to locations selected are paired together and plotted against each other by a scatter generator 14 to result in a two-dimensional scatter plot and displayed to the operator on a scatter plot display device 15. The image data set data value is graphed against the gradient data set data .value corresponding to the same (x,y,z,t) parameter selected. The displayed points in such a scatter plot tend to fall into clusters representing the different tissue types. If each entry of the data values sets is labeled with an identification of the tissue type from which it is selected, then the clusters of data points can be identified with the corresponding tissue types. Moreover, additional locations selected during training provide a more uniform distribution of such sample data points over the tissues of interest, and reduce the number of locations having ambiguous-tissue types. Thus, iterative sequencing of the use of slice display unit 13, scatter generator 14, scatter plot display 15 and pointing device 16 petits the selection of a uniform distribution of sample points over all of the tissue classes of interest within a reasonable period of time. It has been found, for example, that an experienced user can obtain forty uniformly distributed sample data points for each of five different tissue classes in approximately five minutes.

Once an adequate number of sample locations have been selected and plotted, the data values and tissue type corresponding to each selected location are supplied to a probability calculator 17. Calculator 17 calculates a probability distribution for each tissue type for the selected locations and corresponding data values plotted on scatter plot. It is assumed that the recorded intensity values include random errors and that the position of each tissue in the data space follows a bivariate normal probability distribution. It is then possible to use the selected locations and data values to calculate the probability distribution for each tissue type, using the sample data values and locations as representative of the various tissue types.

Figure 2:
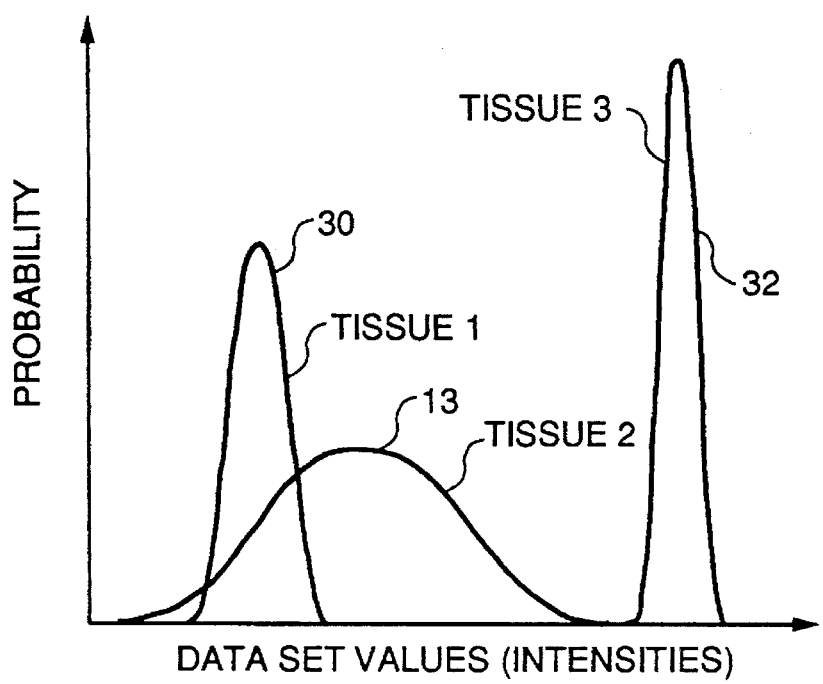
FIG. 2 is a typical two-dimensional, single variate probability distribution for each of three tissues of interest in a single slice of data from a non-intrusive data gathering system, useful in understanding the data segmentation system of the present invention.

A typical two-dimensional, single variate probability distribution for three tissue classes is shown in FIG. 2. A first tissue type, 30, has a probability distribution overlapping the probability distribution for a second tissue type 31. A third tissue class, 32 has a probability distribution which does not overlap that of the first two tissue types.

Figure 3:
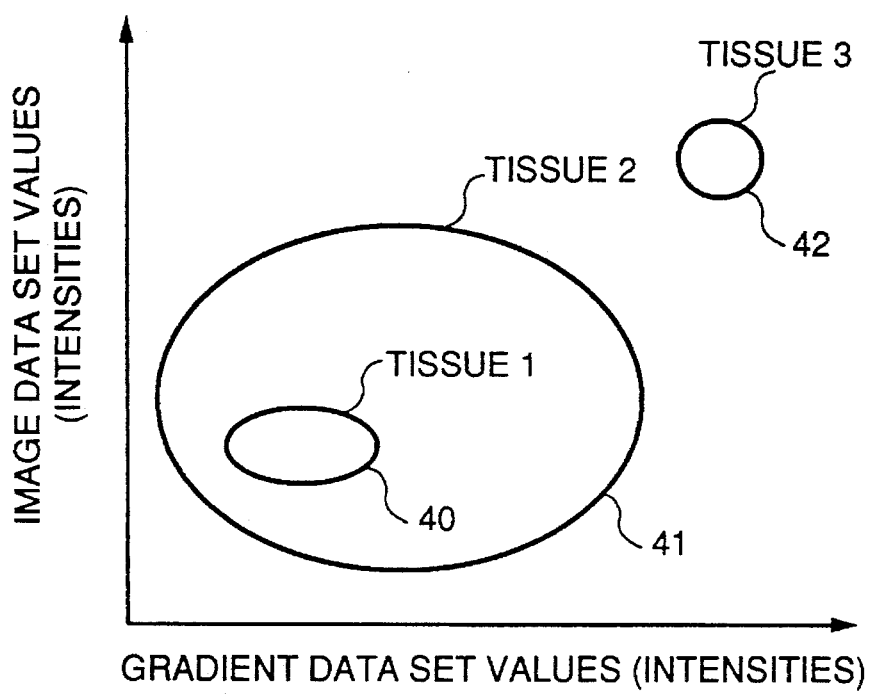
FIG. 3 is a typical scatter plot of a single slice of two independent data sets from a non-intrusive data gathering system showing the clustering of data points from different tissues and useful in selecting sample data points for the data segmentation process of the present invention.

Extending these probability distributions to three dimensions, and using bivariate probabilities, is straightforward. The corresponding scatter plot is shown in FIG. 3 where tissue data duster 40 corresponds to tissue type 1 and probability 30 (FIG. 2), tissue data cluster 41 corresponds to tissue type 2 and probability 31 and tissue data cluster 42 corresponds to tissue type 3 and probability 32. It can be seen that identifying additional data points distributed throughout a tissue cluster is readily accomplished, using the scatter plots.

More specifically, for the two-fold data set of illustrative embodiment, the bivariate normal probability distribution can be represented by $f_i(x_1, x_2,)$ where i is the tissue class identification, $x_1$ represents the data samples from image data set for the ith tissue, from image data storage device 3, and $x_2$ represents the data samples from the gradient data set for the ith tissue, from data store 7. The function fi depends on the deviates $X_1$ and $X_2$ of the sampled data values from the mean data values $<x_1>_i$ and $<x_2>_i$ for each data cluster representing a different tissue class. In accordance with standard statistical analysis, $$X_1 = x_1 - <x_1>_i \qquad (1)$$

$$X_2 = x_2 - <x_2>i$$

and the variances $\sigma_1, \sigma_2$ and the correlation $\rho$ are given by $$\sigma_1^2 = \frac{\Sigma X_1^2}{N} \qquad (2)$$

$$\sigma_2^2 = \frac{\Sigma X_2^2}{N}$$

$$\rho \sigma_1 \sigma_2 = \frac{\Sigma X_1 X_2}{N} \qquad (3)$$

The probability distribution is then given by $$f_i(x_1, x_2) = \frac{e^{(-Q/2)}}{A} \qquad (4)$$

where Q is a quadratic form in the deviates given by $$Q_1 = \frac{1}{(1-\rho^2)} \left[ \frac{x_1^2}{\sigma_1^2} - \frac{2\rho x_1 x_2}{\sigma_1 \sigma_2} + \frac{x_2^2}{\sigma_2^2} \right] \quad (5)$$

The amplitude A is chosen to make the total probability unity, i.e., $$A_i = 2\pi\sigma_1\sigma_2 \sqrt{(1-\rho^2)} \quad (6)$$

A bivariate normal distribution is a Gaussian with an elliptical cross section given by setting Q equal to a constant. The shape of the ellipse depends on the variances $\sigma_1$ and $\sigma_2$ and the correlation $\rho$. If the variables $x_1$ and $x_2$ are not correlated, the distribution function becomes a circular Gaussian in the sample space.

Any number n of three-dimensional data sets with different contrasts can be used to calculate a multivariant normal distribution by extending the probability function $f_i(x_1, \ldots, x_n)$ to the higher dimensions. The quadratic form $Q_i$ then becomes $$Q_i = \frac{1}{2} X'S^{-1}X \quad (7)$$

where X and X' are the n dimensional deviate vector and transpose vector and S is the covariance matrix with elements $$[S_{1m}] = \frac{\Sigma X_1 X_m}{N} \quad (8)$$

The amplitude then becomes $$A_i = (2\pi)^{N/2}|S|^{1/2} \quad (9)$$

Increases in the number of data sets improve the tissue class segmentation and provide a richer set of alternative data values for surface calculations.

Once the probability calculation is completed for the scatter plot data values, probability calculator 17 of FIG. 1, stores the three-dimensional probability distribution in a 3D scatter plot storage device 51.

More particularly, the 3D scatter plot is calculated by probability calculator 17 as given by $$f_i(x_1,x_2) > f_j(x_1,x_2) \quad (10)$$

for all tissue classes j not equal to tissue class i. Substitution of the probability distribution from equation (4) into equation (10) and taking the natural logarithm, gives the relationship $$2\ln(A_i) + Q_i < 2\ln(A_j) + Q_j \quad (11)$$

Equation (11) provides an easily applied classification algorithm which minimizes the total of the percentage errors of each tissue. It differs from Bayes' Rule in that each probability function is not weighted by the fraction of each tissue in the total volume. It is not possible, however, to use Bayes' Rule for classifying this 4D data because the tissue volumes are not known before segmentation. It is therefore assumed that each tissue has an equal weight.

The 3D scatter plot thus generated can be used directly to identify the tissue types of data sets in data storage devices 3 and 7. An address generator 50 simultaneously produces addresses for locations which do not yet have a tissue type associated with them to data storage devices 3 and 7 which provide these data values to a feature map generator 53.

Feature map generator 53 interacts with 3D scatter plot storage device 51 to plot the data values it receives on the 3D scatter plot to ascertain which tissue type has the highest probability at the plotted point. An appropriate tissue type is assigned to a data value representing a given location and stored in a segmented data store 55. In a final display, these tissue type identifier tags may be used in color coding various tissues types.

Mis-classified pixels, however, appear as regions of incorrect coloring, indicating that the original samples did not fully segment the data. The segmentation can be improved by adding some corrected sample points to the original set and recalculating the probability distributions with probability calculator 17.

The tissue types and corresponding locations may optionally be subjected to filtering in a feature filter 56 to remove randomly mis-classified data values. A filter 56, shown in phantom, is designed to approximate a three-dimensional diffusion suitable for smoothing interfaces between tissue types. Tissue assignments and corresponding locations, which may have been filtered, are passed to connectivity calculator 57 such as that described in the aforementioned article entitled "3D Reconstruction of the Brain from Magnetic Resonance Images Using a Connectivity Algorithm," by H. E. Cline et al., published in Magnetic Resonance Imaging, Vol 5, No. 5, pages 345–352, 1987. A connectivity calculator 57 starts with a given location in a tissue type and determines contiguous adjacent tissue with a similar tissue type thereby segmenting locations and data values into solid structures.

Once tissue within the subject have been segmented into solid structures, measurement of volumes may be determined. Operator 2 interacts with an input device 60 to select from a variety of vascular parameters to be calculated, and where applicable, locations, and cardiac cycle time instants for which the parameters are to be calculated. The operator selections are provided to a functionality calculator 58. Functionality calculator may employ monitor means 61 in addition to input device 60 to communicate with operator by providing menus and other prompts. For example, operator 2 may select that the volume of the left ventricle be determined over an entire cardiac cycle from a menu. Functionality calculator 58 receives segmented data from connectivity calculator 57 and calculates the volume inside the left ventricle over the specified cycle. The volume may be calculated by determining the area of each slice, and with knowledge of the slice thickness, approximate the volume. The difference between largest and smallest volumes of the left ventricle will indicate cardiac output per cardiac cycle. Functionality calculator 58 may also determine ejection fraction my comparing the volumes of various heart chambers over the cardiac cycle. Functionality calculator 58 may also determine unusually enlarged heart, an thinning of vessel walls indicating the possibility of an embolism. Other cardiac measurements may become obvious in light of structure segmentation, accurate measurement of volumes of blood, muscle tissue, and color coded anatomy.

In alternative embodiments, any or all of the scatter plot display 15, slice display unit 13, and monitor means 61 may share the same display device. Also, input device 60 and pointing device 16 may be the same device.

Figure 4:
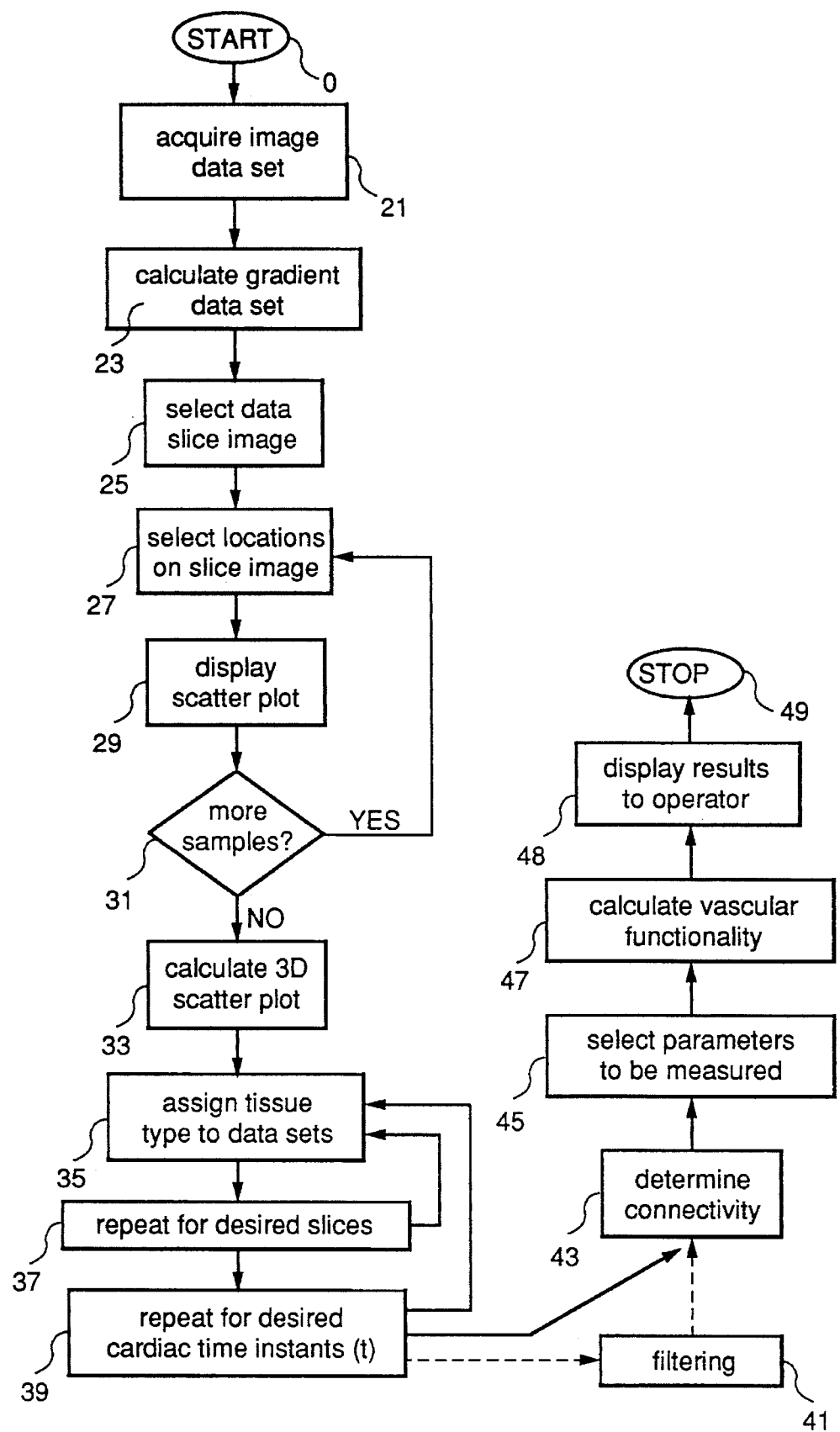
FIG. 4 is a flow chart of the steps of a data segmentation process practiced with the system of FIG. 1.

The vascular functionality measurement system of FIG. 1 requires a minimum of intervention by the human user and produces a high quality feature map almost entirely automatically. The procedure for implementing data segmentation using the system of FIG. 1 is shown in FIG. 4, which is a flowchart of the data segmentation process using the system of FIG. 1. From a starting point 20, 4D image data set (x,y,z,t) is acquired of a subject in step 21 by a non-invasive imaging device. This 4D image data set represents 3-dimensional data acquired by cardiac gating at cardiac time instants (t) throughout the cardiac cycle of the subject. The 4D image data set is passed through a gradient calculation unit to define a gradient data set at step 23. The gradient data set is a measure of spatial changes of the image data set values for each cardiac instant (t). A slice image is displayed to an operator from image data set for a specific cardiac instant (t) at step 25. For example, this may be defined as all data for a specified (y,t). The operator selects locations on the displayed slice image at step 27. Data values from the image data set and gradient data set corresponding to the locations selected by the operator are displayed against each other on a scatter plot at step 29 to the operator. Afar viewing the displayed scatter plot, the operator decides at decision step 31 whether any more samples are needed to discriminate all of the tissues of interest and to provide uniform sample distribution within the tissues of interest. If more samples are needed, steps 27, 29 are repeated to select more locations and data values, and display the new scatter plot to the operator. If no more samples are required, the bivariate probability distribution, or 3D scatter plot, is calculated from the selected locations and data values at step 33, using equation (4).

The 3D probability distribution is employed by a feature map generator which analyzes each data value of the image data set and gradient data set for the current data slice and assigns a tissue type to these data values in step 35 creating a feature map. The process is repeated for other desired slices in the data sets at step 37, and for other desired cardiac instants (t) at step 39.

Optionally, filtering may be performed to reassign misassigned locations at step 41. At step 43 the assigned values, whether filtered or not, may be processed to determine connectivity of similar tissue types belonging to the same structure, having the same, or similar tissue type assignments. This results in solid structures, with defined boundaries between adjacent structures. This accurate segmenting causes subsequent measurements to be much more accurate than the prior art.

At step 45, the operator selects which vascular parameters to be calculated, and if required structures to be measured. Many of the vascular parameters deal with the measurement of cardiac chambers throughout the cardiac cycle.

In step 47 the desired functionality is calculated and the results of the calculated vascular parameters are displayed at step 48 in an appropriate fashion, which may include a time-lapse movie of a slice of the subject's heart over the cardiac cycle, or actual numerical data by cardiac time instant (t).

The process terminates at step 49.

While only certain preferred features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A vascular functionality measurement system for determining vascular functionality of a living subject at specific points within the cardiac cycle of the subject comprising:

a) a non-invasive imaging device for acquiring an image data set wherein said data set includes a plurality of data values at different locations within said subject;

b) an image data storage device coupled to the non-invasive imaging device for storing the image data set;

c) a gradient calculation unit for creating a spatial gradient data set from the image data set having data values representing a spatial change in the image data set data values;

d) a gradient data storage device for storing the gradient data set;

e) a slice display unit for displaying a slice image from selected data values from the image data set;

f) a pointing device for interacting with an operator for selecting a plurality of locations characteristic of a tissue type;

g) scatter generator for creating a scatter plot of each data value of the image data set against the data value of the gradient data set for each selected location;

h) a probability calculator for calculating a spatial probability distribution for the data values of the scatter plot;

i) a feature map generator for assigning the data values of all remaining locations not selected, to a tissue type having the maximum probability distribution at that location;

j) a connectivity calculator for grouping data values corresponding to contiguous locations assigned to the same tissue type as separate internal structures; and k) functionality calculator for determining desired vascular functionality by measuring structure volumes at specific times (t) during said subject's cardiac cycle.

2. The vascular functionality measurement system of claim 1 further comprising a scatter plot display coupled to the sample data store for plotting and displaying the data set values of the 3D data set against the gradient data set for the selected locations as a scatter plot diagram to aid an operator in selecting additional locations of a desired tissue type.

3. The vascular functionality measurement system of claim 1, wherein the non-invasive imaging device comprises a magnetic resonance (MR) imaging means gated according to the subject's cardiac cycle for gathering said image data set.

4. The vascular functionality measurement system of claim 1, wherein the non-invasive imaging device comprises a computed axial tomography (CAT) means gated according to the subject's cardiac cycle for gathering said image data set.

5. The vascular functionality measurement system of claim 1, further comprising filter means coupled to the connectivity calculator for receiving the grouped data values and corresponding tissue type assignments and re-assigning the data values of the image data set at locations corresponding to a boundary between different adjacent tissue types, to tissue types causing a smoothing of the boundary, and providing the re-assigned tissue types, grouped data values and corresponding locations to the functionality calculator via the connectivity calculator.

* * * * *